US010144917B2

United States Patent
Rosa-Calatrava et al.

(10) Patent No.: US 10,144,917 B2
(45) Date of Patent: Dec. 4, 2018

(54) METHOD FOR PREPARING A VACCINE ANTIGEN, RESULTING VACCINE ANTIGEN AND USES

(71) Applicants: CALIXAR, Lyons (FR); Université Claude Bernard Lyon 1, Villeurbanne (FR); Hospices Civils de Lyon, Lyons (FR); INSERM, Paris (FR)

(72) Inventors: Manuel Rosa-Calatrava, Lyons (FR); Aurélien Traversier, Vénissieux (FR); Élodie Desuzinges-Mandon, Saint-Genis-Laval (FR); Emmanuel Dejean, Solaize (FR)

(73) Assignees: CALIXAR, Lyons (FR); UNIVERSITÉ CLAUD BERNARD LYON 1, Villeurbanne (FR); HOSPICES CIVILS DE LYON, Lyons (FR); INSERM, Paris (FR)

( * ) Notice: Subject to any disclaimer, the term of this patent is extended or adjusted under 35 U.S.C. 154(b) by 16 days.

(21) Appl. No.: 15/507,620

(22) PCT Filed: Aug. 28, 2015

(86) PCT No.: PCT/FR2015/052285
§ 371 (c)(1),
(2) Date: Aug. 9, 2017

(87) PCT Pub. No.: WO2016/030635
PCT Pub. Date: Mar. 3, 2016

(65) Prior Publication Data
US 2017/0362578 A1 Dec. 21, 2017

(30) Foreign Application Priority Data
Aug. 29, 2014 (FR) ..................... 14 58124

(51) Int. Cl.
C12N 7/02 (2006.01)
A61K 39/145 (2006.01)
C07C 39/17 (2006.01)
C12N 7/04 (2006.01)
A61K 39/12 (2006.01)
(Continued)

(52) U.S. Cl.
CPC ........... *C12N 7/04* (2013.01); *A61K 39/12* (2013.01); *A61K 39/145* (2013.01); *C07C 39/17* (2013.01); *C12N 7/00* (2013.01); *A61K 2039/5252* (2013.01); *C12N 2760/16134* (2013.01); *C12N 2760/16151* (2013.01)

(58) Field of Classification Search
None
See application file for complete search history.

(56) References Cited

U.S. PATENT DOCUMENTS 4,206,014 A    6/1980 Reichert et al.
6,048,537 A    4/2000 Violay et al.
(Continued)

FOREIGN PATENT DOCUMENTS

WO    9936085 A1    7/1999
WO    0228422 A2    4/2002
(Continued)

OTHER PUBLICATIONS

Matar-Merheb et al. Structuring Detergents for Extracting and Stabilizing Functional Membrane Proteins. PLoS ONE 6(3): e18036. 2011.*
(Continued)

*Primary Examiner* — Nianxiang Zou
(74) *Attorney, Agent, or Firm* — Cantor Colburn LLP (57) ABSTRACT

The present invention relates to a method for preparing a vaccine antigen, which includes a step of fragmenting a biological membrane associated with said vaccine antigen by treating said biological membrane with at least one calixarene of formula (II): wherein: X is a —(CH2)-CO2Y group and Y is an alkaline metal or one of the pharmaceutically acceptable salts thereof, wherein said resulting vaccine antigen also includes a fragment of the biological membrane associated with said antigen. The present invention also relates to a vaccine that can be produced by implementing the method, including a calixarene of formula (II) in carrier format, with a quantity of 0.1 to 1,000 μg in the total weight of the vaccine. The present invention further relates to the use of a calixarene as defined above for the preparation of a vaccine or a vaccine antigen, and to the vaccine for use as a drug in the treatment or prevention of an infectious disease.

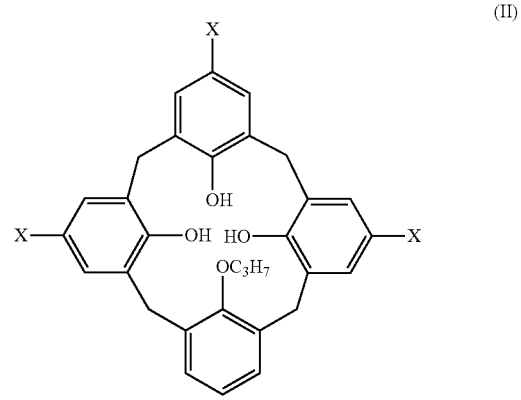

11 Claims, 4 Drawing Sheets (51) Int. Cl.
    *C12N 7/00* (2006.01)
    *A61K 39/00* (2006.01)

(56) References Cited

U.S. PATENT DOCUMENTS

| | | | |
|---|---|---|---|
| 8,481,691 B2 * | 7/2013 | Coleman | B01D 11/0492 |
| | | | 530/350 |
| 2009/0006950 A1 | 1/2009 | Gross et al. | |
| 2011/0014230 A1 | 1/2011 | Haussmann et al. | |

FOREIGN PATENT DOCUMENTS

| | | |
|---|---|---|
| WO | 0228426 A1 | 4/2002 |
| WO | 02067983 A1 | 9/2002 |
| WO | 02090533 A2 | 11/2002 |
| WO | 2005058357 A1 | 6/2005 |
| WO | 2005113756 A1 | 12/2005 |
| WO | 2008092153 A2 | 7/2008 |
| WO | 2008129058 A1 | 10/2008 |
| WO | 2009029695 A1 | 3/2009 |
| WO | 2009115917 A2 | 9/2009 |
| WO | 2009144419 A1 | 12/2009 |
| WO | 2011051235 A1 | 5/2011 |

OTHER PUBLICATIONS

A. H. Ellebedy et al. "Influenza Vaccines" Vaccine, Nov. 5, 2009, vol. 27, pp. 1-9.
Audrey La Ru et al. "Scalable production of influenza virus in HEK-293 cells for efficient vaccine manufacturing", Vaccine, 2010, vol. 28, pp. 3661-3671.
George K. Hirst "The Quantitative Determination of Influenza Virus and Antibodies by Means of Red Cell Agglutination", J. Exp. Med., 1942, vol. 75, pp. 47-64.
Guillaume Lenoir et al. "Overproduction in yeast and rapid and efficient purification of the rabbit SERCA1a Ca2+-ATPase", Biochimica et Biophysica Acta, 2002, vol. 1560, pp. 67-83.
Jonas E. Salk "A Simplified Procedure for Titrating Hemagglutinating Capacity of Influenza-Virs and the Corresponding Antibody", J. Immunol, 1944, vol. 49, pp. 87-98.
Michel Ollivon et al. "Vesicle reconstitution from lipid-detergent mixed micelles", Biochimica et Biophysica Acta, 2000, vol. 1508, pp. 34-50.
Milton J. Rosen "Micelle Formation by Surfactants", Surfactants and Interfacial Phenomena, 2004, pp. 105-113.
Geraci Corrada et al. "First Self-Adjuvant Multicomponent Potential Vaccine Candidates by Tethering of Four or Eight MUC1 Antigenic Immunodominant PDTRP Units on a Calixarene Platform: Synthesis and Biological Evaluation", Bioconjugate Chemistry, Oct. 16, 2013, vol. 24, No. 10, pp. 1710-1720.
International Search Report dated Nov. 25, 2015 re: Application No. PCT/FR2015/052285; pp. 1-3, citing: WO 2009/144419 A1, WO 2009/029695 A1, WO 2011/051235 A1 and Corrada et al.
Written Opinion dated Nov. 25, 2015 re: Application No. PCT/FR2015/052285; pp. 1-6; citing: WO 2009/144419 A1, WO 2009/029695 A1, WO 2011/051235 A1 and Corrada et al.

* cited by examiner

METHOD FOR PREPARING A VACCINE ANTIGEN, RESULTING VACCINE ANTIGEN AND USES

TECHNICAL FIELD

The present invention relates to a process for preparing a vaccine antigen comprising a membrane protein, and also to a vaccine antigen and a vaccine, and to uses thereof.

The present invention has an industrial use in the medical field and in particular in the vaccine preparation field.

In the description below, references between brackets ([ ]) refer back to the list of references presented at the end of the text.

BACKGROUND

Vaccination consists in immunizing a person or an animal against an infectious disease, generally by administering a vaccine to a person or animal. Vaccines, which stimulate the immune system, protect the person or animal against an infection or a disease.

It is established that human vaccination thus makes it possible to combat and eliminate potentially deadly infectious diseases, and it is estimated that in this way more than 2 to 3 million deaths per year are prevented. It is one of the most profitable investments in the health field.

A vaccine is an antigenic preparation which makes it possible to induce, in the person or animal vaccinated, a pathogenic agent-specific immune response capable of protecting them against natural infection or of attenuating the consequences thereof.

The flu is a common viral respiratory infection, and seen throughout the world, which evolves in epidemic winter episodes in tempered regions, due to influenza viruses. The World Health Organization (WHO) considers that they cause between 3 and 5 million serious cases and 250 000 to 500 000 deaths per year worldwide (http://www.pasteur.fr/fr/institut-pasteur/presse/fiches-info/grippe#sthash.PwUNmJ10.dpuf). The influenza viruses responsible for pathological conditions in humans are the type A and B influenza viruses. While type B influenza viruses circulate in the lineage form, type A influenza viruses are categorized in viral subtypes according to the antigenic properties of the major two surface glycoproteins, hemagglutinin (HA) and neuraminidase (NA). Influenza viruses have between 300 and 800 glycoproteins at their surface associated with an NA/HA ratio that can range from one to ten.

The viruses circulating in humans and responsible for seasonal epidemics are the viruses A (H1N1) and A (H3N2). Since the main reservoir of influenza viruses is the animal reservoir (avian and porcine), animal viruses can cross the species barrier and infect humans. Viruses such as avian virus A (H5N1) and pandemic virus A (H1N1) can cause serious public health problems.

In point of fact, vaccination is for the moment the only effective means for protecting populations against influenza viruses. The "seasonal" vaccine makes it possible to acquire immunity against the seasonal circulating viruses A such as (H1N1) and (H3N2) and the various lineages of virus B. It is defined each year on the basis of the prototype strains of the prior year and contains the antigens of the type A and type B seasonal viruses. The host's immune response is mainly of humoral type with expression of neutralizing antibodies that are directed against the HA and NA proteins for the viruses.

Because of a considerable antigen shift in these two proteins, the vaccine composition must be re-evaluated annually.

The conventional process for producing a vaccine is based firstly on obtaining, by genetic reassortment between the A/PR8/34 (H1N1) strain and the seasonal virus strains, vaccine seeds on eggs, for each of the annual prototype A strains determined by the WHO. Most vaccine manufacturers usually use these reassortment viruses deriving mainly from the parental A/PR/8/34 virus. Thus, each vaccine seed is derived from a process of genetic reassortment between the prototype A strain and the A/PR8/34 (H1N1) virus which possesses optimal replicating capacities in eggs. The production of this type B virus is carried out directly on eggs without reassortment with PR8.

The viral particle contains eight distinct gene segments, consisting of a single RNA chain linked to nucleoproteins and associated with a polymerase complex, each of the genes encoding one to three given proteins of the virus: HA, NA, M1, M2, NP, NS1, NEP, PB1, PB1F2, PB1N40, PB2 and PA. Consequently, a long selection process makes it possible to obtain the vaccine reassortment, comprising at least the gene segments encoding HA and NA of the prototype strain on the genetic background of the PR8 virus ("6+2" composition). The 2 vaccine reassortants, resulting from the genetic reassortment between the 2 prototype strains and the parental A/PR/8/34 strain, are then amplified on eggs. The HA and NA antigens are extracted from allantoic productions, and optionally combined with adjuvants in order to produce the vaccine doses.

This industrial process for the production of vaccine doses is long (4 to 6 months). However, in the case of the production of pre-pandemic vaccines, in particular against human flu, it has been evaluated by the WHO that approximately 1 billion people would have to be vaccinated if a plan for combatting a flu pandemic was to be implemented. In point of fact, such a combatting plan will depend partly on the efficiency of the bulk and rapid production of vaccines.

In order to face up to the increasing demand for vaccines against the seasonal circulating strains, but also to the demand—that is difficult to predict—for vaccines against one (or more) potentially pandemic emerging strains, the availability of eggs may prove to be a limiting factor, all the more so since risks of avian pandemics in livestock persist. There is, however, a constant difficulty of producing a good yield of B strains in eggs, and also some type A reassortants which are not 6+2 but instead 5+3 or 4+4.

Thus, in order to reduce the time between the selection of the circulating prototype strains and the production of the vaccine doses, alternative strategies have been developed. Influenza viruses can also be produced in cell systems (Barrett P N, Portsmouth D, Ehrlich H J. Developing cell culture-derived pandemic vaccines. Curr Opin Mol Ther. 2010 February; 12(1):21-30 ([1]); Le Ru A, Jacob D, Transfiguracion J, Ansorge S, Henry O, Kamen A A. Scalable production of influenza virus in HEK-293 cells for efficient vaccine manufacturing. Vaccine. 2010 May 7; 28(21):3661-71 ([2])). The production of vaccine strains and also the amplifications thereof can be carried out on cells using industrial bioreactors. Indeed, the use of a cell line for amplifying vaccine strains makes it possible, inter alia, to no longer be dependent on the "egg" system (amount of egg and production yield insufficient for managing a pandemic), reduces the surface antigen modifications regularly observed in allantoic production and does not cause allergies. This strategy makes it possible to more readily meet the vaccine demand during the emergence of a pandemic influenza virus (for example A H1N1).

Nevertheless, these systems, and in particular the registered cell lines (MDCK, Vero, PERC6, EB66, etc.) do not allow optimal replication of influenza viruses, thereby constituting a major limiting factor in terms of vaccine seed production. Production yields in cell systems are still currently lower than those obtained in the allantoic system. Thus, at the current time, few manufacturers have chosen this new production method since the industrial process is far from being as effective as eggs for the moment.

In order to reduce as much as possible the vaccine dose production time and with the objective of having an equivalent yield level, in terms of number of doses, the obtaining of the vaccine seeds can be carried out by using reverse genetic techniques, making it possible to more rapidly obtain the vaccine reassortant of "6+2" composition, thus eliminating all the selection steps. The production of recombined viruses by reverse genetics provides the most realistic alternative for efficiently meeting vaccine demand. The production of recombined viruses by reverse genetics provides the possibility, secondly, of producing an "optimized" PR8 virus making it possible, when it is used by means of a process of genetic reassortment with prototype strains, to produce vaccine reassortants having optimized viral characteristics for in-egg or in-cell vaccine dose production. This type of method can also be applied for in-cell production.

Another strategy for optimizing vaccine production in allantoic and cell systems is aimed at increasing the yield of the viral production on the basis of genetic modifications of the vaccine seeds and/or using small chemical molecules of interest targeting the host cell. Such processes are undergoing evaluation (FR 10/55716 ([3]), WO 2012007380 ([4]), FR 10/59132 ([5]), WO 2012059696 ([6])).

Another strategy consists in improving the efficacy of the vaccine antigens, by adding adjuvants, thereby making it possible to produce more vaccine doses for the same limited number of eggs and the same amount of glycoproteins produced (Ellebedy A H, Webby R J. Influenza vaccines. Vaccine. 2009 Nov. 5; 27 Suppl 4:D65-8 ([7])). This process is more recommended for people with a deficient immune system. Moreover, public opinion is rather refractory to the use of adjuvants.

Finally, one strategy consists in optimizing the step of extracting the vaccine antigens ("split") downstream of the production process: the objective being to obtain better and more extraction of the vaccine antigens while more effectively preserving their conformational structure and thus their antigenic property on which the protective power of the vaccine is directly dependent.

More specifically, the viral production obtained using infected embryonic hen eggs (harvesting of the allantoic fluid) or using culture of infected cell lines in a bioreactor (harvesting of the culture medium) is purified on a sucrose gradient and then inactivated by chemical treatment (preferentially with formalin, for obtaining according to the regulations a drop in the viral titer of 15 logs). The process subsequently involves the use of a detergent that will disrupt/fragment ("disrupting/fragmenting") the viruses ("split virions") and purification of the vaccine antigens by diafiltration.

The split, or fragmented virus, obtained is combined with partial or total solubilization of the viral proteins, thus modifying the (infectious) integrity and function of the viruses. Splitting also constitutes a method of inactivation supplementary to the chemical method; the term orthogonal inactivation is then used.

The split can be obtained by treating the purified viruses with various detergents, in particular with non-ionic and ionic (e.g. cationic) surfactants, such as: alkylglycosides, alkylthioglycosides, acyl sugars, sulfobetaines, betaines, polyoxymethylene alkyl ethers, N,N-dialkyl-glucamides, hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, DOT-MA (dodecyltrimethylammonium bromide), octyl- or nonylphenoxy polyoxyethanols (e.g. Triton X-100 or Triton NI 01), polyoxymethylene sorbitan esters (Tween surfactants), polyoxyethylene ethers, ethyl ether, polysorbate 80, deoxycholate, Tergitol® NP9, etc.

In this respect, numerous methods for splitting (fragmentation) of influenza viruses are known. Document WO 02/28422 ([8]) describes for example a splitting method by means of a splitting agent chosen from laureth 9, NaDOC, Sarcosyl group, Tween 80™ and Triton X100. Document WO 02/067983 ([9]) describes for its part a splitting method by means of sodium deoxycholate.

Surfactants (or detergents) are amphiphilic molecules composed of clearly distinct polar and nonpolar domains having a marked solubility in water. Beyond a precise concentration called the Critical Micelle Concentration (CMC), the micellization phenomenon is directed by the hydrophobic effect (M. Rosen, "Surfactants and Interfacial Phenomena", 3rd Ed., Hoboken: John Wiley & Sons, Inc., 2004 ([10])).

The nature of the hydrophobic tail, its length, its degree of unsaturation and of branching, the presence or absence of aromatic nuclei and the number of chains affect the chemical properties of the surfactant monomers and their self-assembly in aqueous solution (CMC, aggregation number, size and nature of the geometric form of the aggregates). The nature of the hydrophilic group (neutral or charged, small or bulky) has a strong impact on the properties of the surfactant and its biological application.

Surfactants are categorized in three major families depending on the nature of their hydrophilic part (A. M. Schwartz, J. W. Perry, J. Berch, "Surface Active Agents and Detergents", vol II, R. Krieger Pub. Co., New York, 1977 ([11])): ionic (cationic or anionic) surfactants, zwitterionic (or amphoteric) surfactants and neutral surfactants. They are often referenced as being either soft or harsh. It is possible to make an order of classification of detergents according to their harshest class to their softest class in this sense: ionic>amphoteric>neutral. Ionic surfactants, such as CTAB, are generally denaturing. They disrupt the intramolecular coulombic interactions of proteins and thus disorganize their three-dimensional conformation.

Zwitterionic surfactants (sulfobetaines, betaines) contain both a positive charge and a negative charge in their hydrophilic part and are electrically neutral.

Neutral surfactants, including in particular alkyl glucosides and polyoxymethylene alkyl ethers are characterized by non-charged hydrophilic heads. They are soft and non-denaturing surfactants which, however, disrupt protein-lipid and lipid-lipid interactions, and have no effect on the intramolecular coulombic interactions of proteins.

Detergents comprising a hydrophilic part of polyethylene glycol type (Triton X100, Brij®, Tween, etc.) are commonly used in biochemistry. They have the disadvantage of being considered to be molecules that are chemically heterogeneous with a variable polymerization index n on their PEG (polyethylene glycol) groups. These batches of commercial detergents are therefore not in the form of a species that is chemically well defined in solution, which can lead to a variation in their physico-chemical properties.

In the current context of the emergence of a pandemic pathogenic virus, an infection, for example a flu infection, could lead to 1.3 to 2 million hospitalizations and from 280 000 to 650 000 deaths in industrialized countries alone (WHO data).

One of the major economic challenges is thus to be able to reduce the cost of manufacturing a vaccine dose (more doses per production and/or reduction in the time for obtaining the same amount of doses).

In this context and from an economical point of view, the search for and development of new optimized processes for producing vaccine seeds are legitimate, in particular in terms (i) of improving production yields, (ii) of reducing time and/or costs, (iii) of producing antigens that are more immunogenic.

DESCRIPTION OF INVENTION

The intent of the disclosure is precisely to meet these needs by providing a process for preparing a vaccine antigen which makes it possible to qualitatively and quantitatively optimize the step of extraction of the vaccine antigens, for example influenza vaccine antigens, in an industrial production process, in particular in a cell or allantoic system.

The applicant has in fact shown, surprisingly and unexpectedly, that a calixarene of formula (I), and advantageously a calixarene of formula (II), or a pharmaceutically acceptable salt thereof, can be used for fragmenting (splitting) a virus, in particular by replacing the detergents conventionally used for fragmenting the membranes, for instance Triton X100 or Tween 80.

The process of the invention has in particular the advantage of having better preservation of the conformation of the membrane glycoproteins such as the surface vaccine antigens. The present invention allows, surprisingly, a better preservation of the conformation of the antigens during the step of fragmenting, in particular of the ("split"), viruses, than with the known techniques.

In this context, its use makes it possible to generate vaccine antigens that are much more efficacious from an immunogenic point of view, and thus to reduce the amounts of antigens required in vaccine batches for an identical or comparable protection.

Additionally, these more efficacious antigens are better preserved, advantageously making it possible to be, entirely or partly, an alternative to the known adjuvants. Alternatively, the calixarenes can be used as adjuvants and/or excipients in a vaccine composition, for improving the properties of the vaccine antigens.

The invention makes it possible in particular to increase the quality and/or the quantity of vaccine antigens produced in comparison with the conventional use of the Triton X100 detergent molecule.

The use of the invention can be adapted to the various modes of production that exist (eggs, i.e. allantoic systems, and cells) but also to the other supplementary methods of production optimization (mentioned above), and also to the modes of production being developed, such as methods involving tobacco leaves, protozoa, this list not being limiting.

Thus, in the context of the present invention, there is described a process for preparing a vaccine antigen, comprising a step of fragmenting a biological membrane associated with said vaccine antigen by bringing said biological membrane into contact with at least one calixarene of formula (I):

wherein
n is an integer equal to 1, 3, 5 or 6;
$R^1$, $R^2$, $R^3$ and $R^4$ represent, independently of one another, a hydrogen atom; a linear or branched (C1-C18) alkyl group optionally substituted with one or more heteroatoms chosen from the group of O, S, N and P atoms; a linear or branched (C1-C18) alkyl group optionally substituted with a —COOR group wherein R is a linear or branched (C1-C4) alkyl group; an aryl group comprising from 6 to 20 carbon atoms;
$X^1$, $X^2$ and $X^3$ represent, independently of one another, a —(CH$_2$)m-COOR' or —SO$_3$ or —(CH$_2$)$_m$PO(OH)O or —(CH$_2$)$_m$—NR'$_3$ group, wherein
m is an integer ranging from 0 to 20,
R' represents a hydrogen atom or a linear or branched (C1-C4) alkyl group;
or a pharmaceutically acceptable salt thereof,
wherein the vaccine antigen is not an HIV (human immunodeficiency virus) antigen or a CMV (cytomegalovirus) antigen.

For the purposes of the present invention, the term "vaccine antigen" is intended to mean any preparation comprising at least one membrane protein capable of being expressed by a virus. The vaccine antigen can also comprise a fragment of a biological membrane. In this respect, the membrane protein may be associated with the biological membrane. The vaccine antigen is also understood to be biological membrane fragments bristling with vaccine antigens, for example on the internal and/or external face of the biological membrane.

The vaccine antigen advantageously allows a stimulation of the immune response of a human or animal individual to whom or to which it is administered, against the virus expressing this antigen and in particular against the membrane protein. The vaccine antigen can advantageously enable total or partial immunization of the individual against the antigen and in particular against the membrane protein.

For the purposes of the present invention, the term "membrane protein" is intended to mean a protein associated with a biological membrane, that is to say either anchored, or integral, not free to diffuse in aqueous media and unstable in these media. Among membrane proteins, mention may for example by made of plasma membrane proteins and intracellular membrane proteins (for instance mitochondrial membrane proteins, reticulum proteins, Golgi proteins, lysosomal proteins, this list not being limiting). The membrane proteins can be polytopic proteins or monotopic proteins. The term "polytopic proteins" is intended to mean proteins which cross the membrane one or more times. The term "monotopic proteins" is intended to mean proteins which interact with just one side of the membrane. The membrane protein can also be an integral or peripheral protein. The term "integral proteins" is intended to mean monotopic or polytopic proteins which interact strongly with the membrane, in particular by hydrophobic interactions. These proteins are also called "intrinsic proteins". The term "peripheral proteins" is intended to mean monotopic proteins which interact weakly with the membrane, that is to say either by electrostatic bonds, or by means of other membrane proteins. These proteins are also called "extrinsic proteins".

The membrane protein can be an antigenic protein expressed by an infectious agent against which a vaccination is desired. It may be a protein of viral or microbiological origin. In other words, the membrane protein can be a protein encoded by the genome of an infectious agent. In this respect, the infectious agent can be a virus, in particular an enveloped virus. When it is a virus, it can be a wild-type or recombinant virus, of any type of strain, chosen from the group comprising:

the orthomyxoviridae virus family, including in particular flu viruses, such as mammalian influenza viruses, and more particularly human influenza viruses, porcine influenza viruses, equine influenza viruses, feline influenza viruses, avian influenza viruses, such as the swan influenza virus, the paramyxoviridae virus family, including respiroviruses (sendai, bovine parainfluenza virus 3, human parainfluenza 1 and 3), rubulaviruses (human parainfluenza 2, 4, 4a, 4b, the human mumps virus, parainfluenza type 5), avulaviruses (Newcastle disease virus (NDV)), pneumoviruses (human and bovine respiratory syncytial viruses), metapneumoviruses (animal and human metapneumoviruses), morbilliviruses (measle virus, distemper virus and rinderpest virus) and henipaviruses (Hendra virus, nipah virus, etc.), the coronaviridae virus family including in particular human coronaviruses (in particular NL63, SARS-CoV, MERS-CoV) and animal coronaviruses (canine, porcine, bovine coronaviruses and avian infectious bronchitis coronavirus), the flaviviridae virus family including in particular arboviruses (tick-borne encephalitis virus), flaviviruses (dengue virus, yellow fever virus, Saint Louis encephalitis virus, Japanese encephalitis virus, West Nile virus including the Kunjin subtype, Muray valley virus, Rocio virus, Ilheus virus, tick-borne meningo-encephalitis virus), hepaciviruses (hepatitis C virus, hepatitis A virus, hepatitis B virus) and pestiviruses (border disease virus, bovine diarrhea virus, swan fever virus), the Rhabdoviridae viruses including in particular vesiculoviruses (vesicular stomatitis virus), lyssaviruses (Australian, European Lagos bat virus, rabies virus), ephemeroviruses (bovine ephemeral fever virus), novirhabdoviruses (snakehead virus, hemorrhagic septicemia virus and hematopoietic necrosis virus), the Togaviridae virus family including in particular rubiviruses (rubella virus), alphaviruses (in particular Sinbis virus, Semliki forest virus, O'nyong'nyong virus, Chikungunya virus, Mayaro virus, Ross river virus, Eastern equine encephalitis virus, Western equine encephalitis virus, Venezuela equine encephalitis virus), the herpesviridae virus family including in particular human herpesviruses (HSV-1, HSV-2, chicken pox virus, Epstein-Barr virus, cytomegalovirus, roseolovirus, HHV-7 and KSHV), the poxviridae virus family including in particular orthopoxviruses (such as in particular camoepox, cowpox, smallpox, vaccinia), carpipoxviruses (including in particular sheep pox), avipoxviruses (including in particular fowlpox), parapoxviruses (including in particular bovine papular stomatitis virus) and leporipoxviruses (including in particular myxomatosis virus), the retroviridae virus family including in particular lentiviruses (including in particular human, feline and simian immunodeficiency viruses 1 and 2, caprine arthritis encephalitis virus or Maedi-Visna disease virus) and retroviruses (including in particular Rous sarcoma virus, human lymphotrophic viruses 1, 2 and 3), this list not being limiting. It can also be a modified, reassortant or prototype virus produced in a cell system by reverse genetics.

It can in particular be a viral glycoprotein such as neuraminidase or hemagglutinin, or the M1 and M2 membrane proteins, nucleoprotein, the influenza virus Non-Structural Protein (NS1), or for example the paramyxoviridae virus F fusion protein, or any other viral protein, in particular any protein associated with a membrane of a virus mentioned above. It can also be a modified viral protein, for instance a mutant of the fusion protein F as described in WO 2010/058100 ([26]) or WO 2010/058099 ([27]).

When the membrane protein is derived from a prokaryotic infectious agent, it may for example be an antigen chosen from the pertactin outer surface membrane antigen from *Salmonella* and the *Bordetella pertussis* pertactin antigen, this list not being limiting.

For the purposes of the present invention, the term "biological membrane" is intended to mean any assembly of molecules into a double sheet separating a cell from its environment, composed of a bilayer of amphiphilic lipids, in particular phospholipids, each membrane lipid consisting of a hydrophilic polar head directed toward the outside of the membrane and a hydrophobic tail directed toward the inside. It may be a membrane of a prokaryotic cell, of a eukaryotic, animal or plant cell, or a virus.

It may for example be a vesicular membrane, for example a membrane of a VLP (Virus Like Particle), as described for example in documents WO 2007/132790 ([29]), WO 1999/036085 ([30]), WO 2005/058357 ([31]), or WO 2008/092153 ([32]), of a lysosome, of an exosome or of a proteoliposome, an endoplasmic reticulum membrane, or a Golgi apparatus membrane, this list not being limiting.

In the case of a eukaryotic cell membrane, it may be a vesicular membrane, a rough endoplasmic reticulum membrane, a Golgi apparatus membrane, a smooth endosplasmic reticulum membrane or a plasma membrane, this list not being limiting. It may be an isolated transgenic host cell derived from a cell line in which one or more vaccine antigens are expressed, for example by recombinant DNA or RNA genetic engineering techniques or by infection of a cell with a viral vector expressing one or more vaccine antigens of interest. Any genetic engineering technique known to those skilled in the art that makes it possible to express a transgene in a cell may be used. It may involve a technique involving the expression of a DNA or an RNA, for example a synthetic coding mRNA, introduced into a cell by transduction, for example by electroporation, microinjection, ultrasound, infection or transfection. The expression may be for example transient and/or inducible and/or constitutive of at least one antigen of interest, for instance described in document WO 02090533 ([33]). The cell may be any cell, in particular with the exception of human embryonic stem cells, for example an isolated human cell—human embryonic stem cells being for example excluded —, or an isolated non-human animal or plant cell. The isolated cell may be derived from a cell line chosen from Vero (ATCC No. CCL-81) such as Vero 76 (ATCC No. CRL-1587), CHO such as CHO-KI (CCL 61, ATCC), BHK such as BHK-21 [C-13] (ATCC® CCL-10™), HELA, perC6® (Crucell), HEK293 (ATCC® CRL-1573™), Sf9 (ATCC, CRL-1711), EBx® (Valneva/Vivalis, described in document WO 2008/129058 ([12])), MDCK, for example MDCK (NBL-2) (ATCC® CCL-34™), this list not being limiting. In the case of a cell isolated from a cell line, the process can comprise the following steps:

the isolated cells are inoculated with a fluid containing the virus,
the virus is propagated in the cells,
the virus thus propagated is collected in the cell culture supernatant,
optionally, the virus thus collected is inactivated,
the virus membrane is fragmented.

In the case of a cell isolated from a cell line, the process of the invention can alternatively comprise the following:

the isolated cells are inoculated with a fluid containing the virus,
the virus is propagated in the cells,
the cells expressing the antigen(s) at their surface are collected,
the membrane, for example the plasma membrane, is isolated from the cells by means of a membrane fractionation method, for example by breaking the cells and sequential centrifugations,
the membrane is fragmented.

Or else alternatively:

the antigen(s) are expressed in an isolated cell by means of a genetic engineering method,
the cells expressing the antigen(s) are amplified,
the cells expressing the antigen(s) at their surface are collected,
the membrane, for example the plasma membrane, is isolated from the cells by means of a membrane fractionation method, for example by breaking the cells and sequential centrifugations,
the membrane is fragmented.

Alternatively, the cell can be derived from an embryonated allantoic system. In this respect, this embryonated system may be of any animal species type, for example a hen's egg, or any other animal, in particular avian, allantoic system, which is permissive to viruses. For example, to obtain embryonated hen's eggs producing a membrane protein as defined above, the steps may be the following:

the virus, for example 200 µl at a concentration of $10^{-3}$ pfu/ml, is inoculated into the allantoic fluid of 11-day-old embryonated eggs from hens raised in a sterile chamber,
these eggs are then incubated for two to three days at approximately 33° C., during which time the virus accumulates in the allantoic fluid,
the eggs are cut and the allantoic fluid where the concentration in infectious agents has been multiplied is suctioned out.

In the case of a viral membrane, it may be an envelope derived by budding of a cytoplasmic or plasma cell membrane of the infected host cell, depending on the viruses and/or the viral origin of the vaccine antigens expressed. In this case, the envelope is a membrane of cytoplasmic or plasma origin of the infected cell, modified by the expression of viral glycoproteins associated with these membranes during viral budding, and the lipids of the envelope are, themselves, of cellular origin. In this case, it may be the membrane of the virus against which a vaccination and/or immunization is desired.

For the purposes of the present invention, the term "calixarene" is intended to mean a supramolecular surfactant of the calixarene family. In this respect, the calixarenes used in the invention can be synthesized by any technique known to those skilled in the art. It may for example involve a process as described in document WO 2009/144419 ([28]).

For the purposes of the present invention, the term "alkyl" is intended to mean a saturated or unsaturated, linear, branched or cyclic, optionally substituted carbon-based radical comprising 1 to 12 carbon atoms. By way of indication, mention may be made of methyl, ethyl, propyl, butyl, isobutyl, pentyl, hexyl, octyl, nonyl, decyl, undecyl and docecanyl radicals and branched isomers thereof. The alkyl group can optionally be substituted with one or more heteroatoms chosen from the group O, S, N and P.

The term "aryl" generally denotes a cyclic aromatic substituent comprising from 6 to 20 carbon atoms. In the context of the invention, the aryl group may be monocyclic or polycyclic, which is optionally substituted. In this respect, mention may be made of benzyl or phenyl.

In the context of the present invention, the term "pharmaceutically acceptable salts" comprises the salts prepared with nontoxic acids or bases depending on the substituents present on the compounds. When the compounds of the invention comprise acid functions, the corresponding salts can be obtained by adding an organic or inorganic base to the compound in neutralized form optionally in the presence of a solvent, which is preferably inert. Examples of addition salts of a base can be the sodium, potassium, calcium, ammonium, amino (organic) or magnesium salts. When the compounds of the invention comprise basic functions, the corresponding salts can be obtained by adding an organic or inorganic acid optionally in a solvent which is preferably inert. Examples of inorganic acid addition salts can be the salts of hydrochloric acid, hydrobromic acid, nitric acid, carbonic acid, monohydrogencarbonic acid, phosphoric acid, monohydrogenphos-phoric acid, dihydrogenphosphoric acid, sulfuric acid, monohydrogensulfuric acid or hydriodic acid. Examples of organic acid addition salts can be the salts of acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid or methanesulphonic acid.

In one particular embodiment, the fragmentation step can be carried out with at least one calixarene of formula (I) in which:

n is an integer equal to 1;
$R^1$, $R^2$, $R^3$ and $R^4$ represent, independently of one another, a hydrogen atom; or a linear or branched (C1-018) alkyl group;

$X^1$, $X^2$ and $X^3$ represent, independently of one another, a —$(CH_2)_m$—COOR' or —$SO_3Y$ or —$(CH_2)_m$—PO(OH)OY or —$(CH_2)_m$—$NR'_3$ group in which
m is an integer ranging from 0 to 20,
R' represents a hydrogen atom;
or a pharmaceutically acceptable salt thereof.

A process for preparing a vaccine antigen comprises a step of fragmenting a biological membrane associated with said vaccine antigen by bringing said biological membrane into contact with at least one calixarene of formula (III):

(III)

in which:
X is a —$(CH_2)_o$—$CO_2Y$ group,
o is an integer from 1 to 3,
$R^4$ is a linear or branched (C1-C4) alkyl group, and
Y is an alkali metal,
or a pharmaceutically acceptable salt thereof,
wherein said vaccine antigen obtained also comprises a fragment of the biological membrane, said fragment being The fragmenting step can be carried out with calixarenes in solution or calixarenes in colloidal aggregates owing to their surfactant property. For the purposes of the present invention, the term "colloidal aggregate" is intended to mean assemblies of a few tens to a few hundred calixarene molecules which become organized according to forces of repulsion with respect to the solvent. Given their nature, calixarenes, for example CALX133ACE, are capable of forming aggregates in an appropriate medium, for instance in water, in an aqueous solution, in an isotonic medium or in a biological medium.

The aggregate can preferably be in the form of micelles. The term "micelle" denotes a spheroidal aggregate of calixarene molecules of formula (I) which become organized as a function of the solvent used. For example, in water or an aqueous solvent, the lipophilic ends face into the micelle while the hydrophilic ends form the interface of the micelle with the solvent. In an organic solvent, for example oil, the arrangement is reversed. The term "liposome" denotes small, artificially produced vesicles consisting in particular of strips of phospholipids, separated from one another by aqueous compartments. They can have a structure very close to that of cell membranes. In the context of the present invention, the term "nanoparticle" means an assembly of a few hundred to a few thousand calixarene molecules of formula (I), resulting in an object of which at least one of the dimensions is nanometric in size, for example between 1 and 300 nm. In the process of the invention, the step of bringing an aqueous suspension comprising the membrane protein to be extracted into contact with the calixarene of formula (I) can optionally be carried out in the presence of at least one co-solute chosen from the group comprising:
i) organic and inorganic salts chosen from the group comprising the pharmaceutically acceptable salts;
ii) small bioactive molecules chosen from the group of amino acids, vitamins, lipids, steroids, carbohydrates or metabolites;
iii) oligomeric bioactive molecules chosen from the group of peptides, oligonucleotides and oligosaccharides;
iv) polymeric biological molecules chosen from the group of proteins, polynucleotides and polysaccharides.

According to one embodiment of the invention, the contacting step can be preceded by a step wherein:
the membrane protein to be extracted or the membrane fraction containing it is dissolved in a buffer solution, and
the calixarene of formula (I) is added according to the temperature, pH and concentration conditions described above.

According to one embodiment of the invention, the contacting step can be followed by a centrifugation step, making it possible to separate the membrane proteins complexed with the calixarenes of formula (I), from the non-complexed membrane proteins.

The membrane proteins complexed with the calixarenes of formula (I) and the non-complex membrane proteins can be separated by centrifugation, for example for 1 h, at 4° C. and at the speed of 100 000 g. The centrifugation conditions will depend on the nature of the protein. Those skilled in the art will know how to choose the optimal centrifugation conditions, for example described in Lenoir, G., Menguy, T., Corre, F., Montigny, C., Pedersen, P. A., Thinès, D., le Maire, M., and Faison, P. (2002) Overproduction in yeast and rapid and efficient purification of the rabbit SERCA1a Ca2+-ATPaSe, Biochim. Biophys. Acta 1560, 67-83 ([13]).

Advantageously, the fragmenting step can be preceded and/or followed by a step of inactivation by any method known to those skilled in the art, for example by means of formaldehyde, by means of beta-propionolactone, by ultraviolet radiation, or inactivation with formalin, optionally followed or preceded by a step of partial purification, for example by ultracentrifugation, as described in documents US 2009/0060950 ([14]) and U.S. Pat. No. 6,048,537 ([15]).

The process of the invention can fall within any conventional industrial vaccine antigen production process, for example the processes described in documents WO 2011/051235 ([16]), US 2011/0014230 ([17]), WO 2002/028426 ([18]), US 2009/0060950 ([14]), WO 02/067983 ([9]), U.S. Pat. No. 4,206,014 ([19]), WO 2009/115917 ([20]) or WO 2005/113756 ([21]), by replacing the compound used for the fragmenting (splitting) with the calixarenes of formula (I) or a salt thereof.

According to one embodiment, a diafiltration step can be carried out. Advantageously, it makes it possible to remove the surfactant or other impurities. This step can be carried out by any method known to those skilled in the art. It may for example be a technique chosen from dialysis, dilution, buffer exchange on a column, an enzymatic action, use of polymers, for example Biobeads, in particular SM2 or Dowex, precipitation, or a technique described by Ollivon et al. (Ollivon M1, Lesieur S, Grabielle-Madelmont C, Paternostre M.: "Vesicle reconstitution from lipid-detergent mixed micelles" Biochim Biophys Acta. 2000 Nov. 23; 1508 (1-2):34-50 ([25])); this list not being exhaustive.

Advantageously, a sterile filtration step can be carried out. Advantageously, this step makes it possible to remove even more impurities. This step can be carried out by any method known to those skilled in the art. It may for example be a filtration, for example through a filtering membrane with a porosity of less than 0.22 µm.

In one embodiment, the process of the invention can also comprise a step of dialyzing said vaccine antigen. Advantageously, this step makes it possible to remove even more impurities. This step can be carried out by any method known to those skilled in art. It can for example be a dialysis through a membrane having a porosity of less than 14 000 daltons.

In one embodiment, the process can also comprise a step of concentrating the membrane protein. This step can be carried out by any method known to those skilled in the art. It can for example be precipitation, for example with PEG (polyethylene glycol) or ammonium sulfate, evaporation, use of concentrators, for example of Amicon® type, for example Centricon® or Centriprep® (Merck Millipore).

The process of the invention can also comprise any step known to those skilled in the art in the preparation of vaccines, for example described in the processes of documents WO 2011/051235 ([16]), US 2011/0014230 ([17]), WO 2002/028426 ([18]), US 2009/0060950 ([14]), WO 02/067983 ([9]), U.S. Pat. No. 4,206,014 ([19]), WO 2009/115917 ([20]) or WO 2005/113756 ([21]).

A vaccine antigen that can be produced by carrying out the process defined above for example wherein the vaccine antigen is not an HIV antigen or a CMV antigen, is also described.

A vaccine comprising a vaccine antigen as described above, for example wherein the vaccine antigen is not an HIV antigen or a CMV antigen, is also described.

The vaccine may be administrable by any known route suitable for the vaccination desired, for example by injection, in particular subcutaneously, intradermally, intramuscularly, orally, intranasally, transepithelial, transdermally, by patch, by mucoadhesive tablet, rectally, for example by suppository.

The vaccine can be a vaccine with adjuvant, of the Pandemrix® type (GSK), Focetria® (Novartis) or Humenza® (Sanofi Pasteur) type, or without adjuvant, of the trivalent Fluviral (GSK) or quadrivalent Fluarix (GSK), Celvapan® (Baxter) or Vaxigrip® (Sanofi Pasteur) type, this list not being limiting. In these examples, the virus is replaced with the vaccine antigen according to the invention. In the case of a vaccine with adjuvant, said adjuvant may be any adjuvant known to those skilled in the art which makes it possible to increase the immune response, for example aluminum salts, lysolecithin, mineral gels, aluminum hydroxide, microemulsions, lipid particles, or oligonucleotides.

The vaccine can comprise any pharmaceutically acceptable carrier, such as those contained in the vaccines mentioned above, or else stabilizing salts, dissolving agents, osmoregulators, thickeners, redox compounds for maintaining a physiological redox potential, this list not being limiting.

A dose of vaccine intended for a human being may for example, correspond to a volume of 0.5 ml to be injected.

The vaccine can also comprise a calixarene of formula (I) in particular in excipient format. With respect to the present invention, the term "excipient" is intended to mean a substance intended to have an acknowledged effect. It can advantageously confer a given conformation, or other particular physical characteristics, on the final product, while at the same time preventing any unwanted interaction, particularly chemical interaction, with the active ingredient. In this respect, the amount of calixarene possibly present in the vaccine can be from 0.1 to 1000 µg, for example between 0.5 and 700 µg, or between 1 and 600 µg or else between 5 and 500 µg.

Another subject of the invention relates to the use of a calixarene or of formula (II) for preparing a vaccine or a vaccine antigen as described above, for example wherein the vaccine antigen is not a vial antigen as described above, except for those of HIV, or an antigen of CMV. The use of a calixarene of formula (I) is also described.

Another subject of the invention relates to a vaccine antigen or a vaccine as defined above, for application thereof as a medicament in the treatment or prevention of an infectious disease, for example wherein the vaccine antigen is not an HIV antigen or a CMV antigen. The infectious disease can for example be a disease caused by one or more of the viruses chosen from:

the orthomyxoviridae virus family, including in particular flu viruses, such as mammalian influenza viruses, and more particularly human influenza viruses, porcine influenza viruses, equine influenza viruses, feline influenza viruses, avian influenza viruses, such as the swan influenza virus, the paramyxoviridae virus family, including respiroviruses (sendai, bovine parainfluenza virus 3, human parainfluenza 1 and 3), rubulaviruses (human parainfluenza 2, 4, 4a, 4b, the human mumps virus, parainfluenza type 5), avulaviruses (Newcastle disease virus (NDV)), pneumoviruses (human and bovine respiratory syncytial viruses), metapneumoviruses (animal and human metapneumoviruses), morbiliviruses (measle virus, distemper virus and rinderpest virus) and henipaviruses (Hendra virus, nipah virus, etc.), the coronaviridae virus family including in particular human coronaviruses (in particular NL63, SARS-CoV, MERS-CoV) and animal coronaviruses (canine, porcine, bovine coronaviruses and avian infectious bronchitis coronavirus), the flaviviridae virus family including in particular arboviruses (tick-borne encephalitis virus), flaviviruses (dengue virus, yellow fever virus, Saint Louis encephalitis virus, Japanese encephalitis virus, West Nile virus including the Kunjin subtype, Muray valley virus, Rocio virus, Ilheus virus, tick-borne meningo-encephalitis virus), hepaciviruses (hepatitis C virus, hepatitis A virus, hepatitis B virus) and pestiviruses (border disease virus, bovine diarrhea virus, swan fever virus), the Rhabdoviridae virus family including in particular vesiculoviruses (vesicular stomatitis virus), lyssaviruses (Australian, European Lagos bat virus, rabies virus), ephemeroviruses (bovine ephemeral fever virus), novirhabdoviruses (snakehead virus, hemorrhagic septicemia virus and hematopoietic necrosis virus), the Togaviridae virus family including in particular rubiviruses (rubella virus), alphaviruses (in particular Sinbis virus, Semliki forest virus, O'nyong'nyong virus, Chikungunya virus, Mayaro virus, Ross river virus, Eastern equine encephalitis virus, Western equine encephalitis virus, Venezuela equine encephalitis virus), the herpesviridae virus family including in particular human herpesviruses (HSV-1, HSV-2, chicken pox virus, Epstein-Barr virus, cytomegalovirus, roseolovirus, HHV-7 and KSHV), the poxviridae virus family including in particular orthopoxviruses (such as in particular camoepox, cowpox, smallpox, vaccinia), carpipoxviruses (including in particular sheep pox), avipoxviruses (including in particular fowlpox), parapoxviruses (including in particular bovine papular stomatitis virus) and leporipoxviruses (including in particular myxomatosis virus), the retroviridae virus family including in particular lentiviruses (including in particular human, feline and simian immunodeficiency viruses 1 and 2, caprine arthritis encephalitis virus or Maedi-Visna disease virus) and retroviruses (including in particular Rous sarcoma virus, human lymphotrophic viruses 1, 2 and 3), this list not being limiting.

For example, in the case of the flu virus, the vaccine can comprise one or more subtypes of influenza virus A chosen from the H1N1, H2N2, H3N2, H5N1, H7N7, H7N9, H1N2, H9N2, H7N2, H7N3 and H10N7 human subtypes, the H1N1, H1N2, H3N1 and H3N2 subtypes of porcine flu, the H7N7 and H3N8 subtypes of canine flu and of equine flu or the H5N1, H7N2, H1N7, H7N3, H13N6, H5N9, H11N6, H3N8, H9N2, H5N2, H4N8, H10N7, H2N2, H8N4, H14N5, H6N5 and H12N5 subtypes of avian flu, or any other human and/or animal reassortant virus. Alternatively, in the case of the flu virus, the vaccine can comprise one or more chosen human subtypes of influenza virus B, for example a lineage chosen from the Victoria lineage and the Yamagata lineage. In the case of influenza virus B, it is a question in particular of the B/Massachussetts/2/2012 or B/Brisbane/33/2008 vaccine strain.

Another subject of the invention relates to the use of a calixarene as defined above, as adjuvant in a vaccine.

The calixarenes defined above can be used for their immunological activity, and more particularly immunomodulatory activity. They can, depending on the subject, the doses, the antigen and the time at which it is administered, cause an immunostimulation.

For the purposes of the present invention, the term "adjuvant" is intended to mean a substance which, when it is administered (swallowed, inhaled, injected, etc.) together with an antigen stimulates, activates, prolongs, reinforces or modulates the immune system, although this substance does not itself have any antigenic property.

In this respect, the amount of calixarene possibly present in the vaccine can be from 0.1 to 1000 µg, for example between 0.5 and 700 µg, or between 1 and 600 µg or else between 5 and 500 µg to the total weight of the vaccine.

In one particular embodiment, the adjuvant can be added to any vaccine, for example to an inactivated or attenuated vaccine, or a split vaccine, regardless of the production process used.

It would be possible for other advantages to become further apparent to those skilled in the art on reading the examples below, illustrated by the appended figures, given by way of illustration.

EXAMPLES

Example 1: Protocol for Extracting the Influenza Vaccine Antigens Using the CALX133ACE and CALX1103ACE Molecules The CALX133ACE and CALX1103ACE molecules (CALX1103ACE being a calixarene in which $R^4$ is a $C_{10}$ alkyl group) are evaluated for their ability to extract the influenza vaccine antigens (produced from a production of the vaccine seed X-179a, H1N1 pandemic 2009) and they are compared with a detergent used by vaccine producers (Triton X100) and two commercial detergents (FC12 and C12E8). Several concentrations, pH and extraction temperature conditions were evaluated.

The quantitative and qualitative evaluation of the vaccine antigen extraction was carried out using the industrial reference tests for measurement of hemagglutinating activity (hemagglutination test: Hirst, G. K. 1942. The quantitative determination of influenza virus and antibodies by means of red cell agglutination. J. Exp. Med. 75:47-64 ([22]) and Salk, J. E. 1944. Simplified procedure for titrating hemagglutinating capacity of influenza virus and the corresponding antibody. J. Immunol. 49:87-98 ([23])) and quantification (SRID; A quantitative, single-radial-diffusion test for immunological studies with influenza virus. Schild G C, Henry-Aymard M, Pereira H G. J Gen Virol. 1972 August; 16(2): 231-6 ([24])) of the antigens extracted.

The conditions tested were those mentioned in table I:

TABLE I

| Condition No. | Molecule tested | Concentration | Temperature | pH PO₄ buffer | Contact time |
|---|---|---|---|---|---|
| 1 | Triton X100 | 4% | Ambient | 7.95 | 1 h |
| 2 | Triton X100 | 4% | 37° C. | 7.95 | 1 h |
| 3 | CALX133ACE | 1% | Ambient | 7.95 | 1 h |
| 4 | CALX133ACE | 1% | 37° C. | 7.95 | 1 h |
| 5 | CALX1103ACE | 1% | Ambient | 7.95 | 1 h |
| 6 | CALX1103ACE | 1% | 37° C. | 7.95 | 1 h |
| 7 | CALX133ACE | 1% | 4° C. | 7.95 | 2 h |
| 8 | CALX1103ACE | 1% | 4° C. | 7.95 | 2 h |
| 9 | Triton X100 | 4% | 37° C. | 7.95 | 1 h |
| 10 | Triton X100 | 4% | 37° C. | 6.74 | 1 h |

After extraction, dialysis of the fragmented antigens (supernatant SN and extraction pellet) against 1×PBS was carried out in the conventional industrial production process (for example [9], [18]) in order to reduce the salt and detergent concentration of the extraction products. Each batch was thus dialyzed. It was determined that the Triton X100 was not completely removed during the dialysis. However, it appeared that the CALX133ACE molecule could be dialyzed, suggesting that it could be present only in trace amounts in a marketed possible vaccine product.

After dialysis, the extraction products were aliquoted and titrated for their hemagglutinating activity (HA). The data are given in table II below:

TABLE II

| Condition | | | | | | Titer in HAU/50 µl | |
|---|---|---|---|---|---|---|---|
| No. | Molecule tested | Concentration | Temperature | pH PO₄ buffer | Contact time | Supernatant | Pellet |
| 10 | Triton X100 | 4% | 37° C. | 6.74 | 1 h | 128 | 16 |
| 1 | Triton X100 | 4% | Ambient | 7.95 | 1 h | 128 | 64 |
| 2 | Triton X100 | 4% | 37° C. | 7.95 | 1 h | 128 | 16 |

TABLE II-continued

| Condition | | | | | | Titer in HAU/50 μl | |
|---|---|---|---|---|---|---|---|
| No. | Molecule tested | Concentration | Temperature | pH PO₄ buffer | Contact time | Supernatant | Pellet |
| B | CALX133ACE | 0.1% | 4° C. | 7.95 | 2 h | 128 | 4096 |
| 7 | CALX133ACE | 1% | 4° C. | 7.95 | 2 h | 512 | 2 |
| 3 | CALX133ACE | 1% | Ambient | 7.95 | 1 h | 512 | 4 |
| 4 | CALX133ACE | 1% | 37° C. | 7.95 | 1 h | 128 | 0 |
| D | CALX1103ACE | 0.1% | 4° C. | 7.95 | 2 h | 64 | 128 |
| 8 | CALX1103ACE | 1% | 4° C. | 7.95 | 2 h | 1024 | 32 |
| 5 | CALX1103ACE | 1% | Ambient | 7.95 | 1 h | 512 | 32 |
| 6 | CALX1103ACE | 1% | 37° C. | 7.95 | 1 h | 512 | 16 |

The results indicate significant hemagglutinating (HA) titers (512 and 1024 respectively) for the fragmented antigens (SN) obtained after extraction with the CALX133ACE and CALX1103ACE molecules at the concentration of 1% under conditions at 4° C. and at pH=7.95. These titers are significantly higher than those obtained for the antigens extracted (SN) according to the conventional protocol using Triton X100.

These results are all the more significant since (i) the hemagglutinating titer obtained is dependent on the CALX133ACE molecule concentration used (0.1% vs 1%) and (ii) the HA titer of the residues of non-extracted antigens (pellet) is inversely proportional to and lower than that obtained with Triton X100. The extraction temperature appears to be an important parameter; the temperature of 4° C. appears to be the optimal temperature for extraction of the vaccine antigens using the CALX133ACE and CALX1103ACE molecules.

These first results clearly indicated that the CALX133ACE molecules were suitable for the extraction of influenza vaccine antigens from batches of virus produced in the allantoic production system used by vaccine manufacturers. These CALX133ACE and CALX1103ACE molecules allow an extraction which is more efficient than that of the conventional one using Triton X100, from a qualitative point of view (more antigens extracted, higher hemagglutinating activity, native profile of antigen oligomerization).

Example 2: Optimization of the Fragmentation of the Vaccine Antigens and Quantification Thereof for Carrying Out an Efficacy Test in a Murine Model The viral production was carried out by inoculation of 11-day-old embryonated hen's eggs with viral inocula (vaccine seed) followed by concentration and purification. The fragmentation was carried out according to the conventional industrial method using Triton X100 (4%), in comparison with the use of CALX133ACE molecules.

The qualitative evaluation of the vaccine antigen extracted is carried out by means of the industrial reference test, which is the measurement of the hemagglutinating activity of said vaccine antigens (activity of the main antigen, hemagglutinin, titer given in UHA/50 ml). The quantitative evaluation is carried out by means of the industrial reference technique, also used by the drug authorities for the validation and marketing authorization of vaccine batches: Single Radial ImmunoDiffusion (SRID, amount of HA in mg/ml). Finally, the quantification of HA by iTRAQ mass spectrometry makes it possible to obtain a relative quantification between the various samples to be compared in an animal test (amount of HA in mg/ml).

The molecules and conditions that were chosen for the fragmentation were:

Triton X100 at 4% for 1 h at 37° C.

The CALX133ACE molecule at 1% for 2 h at 4° C.

The CALX133ACE molecules do not cause any red blood cell hemolysis in the absence of flu antigens during the hemagglutination test. Furthermore, the molecules are dialyzable, thereby implying that it will be possible to limit the CALX133ACE to trace amounts in the sample.

Example 3: Animal Experiments

In a first experiment, several batches of antigens were produced under the optimal production conditions described above, using Triton X100 or the CALX133ACE molecule as splitting agent. Table III below is a summary of the fragmented materials used for the animal test.

TABLE III

| Experimental condition | % residual detergent | Approximate sample volume (μl) | Titer in UHA/50 μl | HA concentration (μg/ml) by SRID quantif | ITRAQ ratio | [HA] corrected by ITRAQ (μg/ml) | Volume to be injected per mouse (μl) For 0.5 μg of HA Ag | Volume to be injected per mouse (μl) For 2.5 μg of HA Ag |
|---|---|---|---|---|---|---|---|---|
| Split Triton X100 4% | 0.36 | 900 | 1024 | 144.83 | Split Triton X100/split | 144.83 | 3.45 | 17.26 |
| Split CALX133ACE 1% | 0.03 | 800 | 4096 | 54.08 | CALX133ACE C = 1.43 | 101.28 | 4.94 | 24.68 |
| Supernatant Triton X100 4% | 0.19 | 1000 | 1024 | 119.21 | Supernatant Triton X100/S CALX133ACE C = 0.93 | 119.21 | | 20.97 |

TABLE III-continued

| Experimental condition | % residual detergent | Approximate sample volume (µl) | Titer in UHA/50 µl | HA concentration (µg/ml) by SRID quantif | ITRAQ ratio | [HA] corrected by ITRAQ (µg/ml) | Volume to be injected per mouse (µl) For 0.5 µg of HA Ag | For 2.5 µg of HA Ag |
|---|---|---|---|---|---|---|---|---|
| Supernatant CALX133ACE 1% | 0.04 | 850 | 1024 | 48.41 | | 128.64 | | 19.43 |

In this first experiment, it was planned to test two amounts of HA antigens for the splits (0.5 and 2.5 µg) and just one for the supernatants obtained by ultracentrifugation of the splits. For each condition, 12 Balb.c mice were immunized twice (on DO and then on D21) intramuscularly (100 µl total). Several blood samples were taken from the animals on DO, D21, D42 and D63 (cardiac punctures and euthanasia). After each blood sample series, the sera from one and the same group were harvested and mixed so as to have sufficient material for carrying out a hemagglutination inhibition (HAI) test in duplicate and also a microneutralization test in duplicate.

The results obtained are given in table IV below:

TABLE IV

| | Preliminary | | Sample 2 | | Sample 3 | | Cardiac puncture | |
|---|---|---|---|---|---|---|---|---|
| | HAI | Microneutralization (MN) | HAI | Microneutralization (MN) | HAI | Microneutralization (MN) | HAI (mean) | Microneutralization (MN) |
| Group 1 split Triton X100 0.5 µg of Ag | <10 | <10 | <10 | <10 | <10 | 20 | <10 | <10 |
| Group 2 split Triton X100 2.5 µg of Ag | <10 | <10 | <10 | <10 | 80 | 80 | 29.17 | 40 g |
| Group 3 split CALX133ACE 0.5 µg of Ag | <10 | <10 | <10 | <10 | 40 | 80 | 25.83 | 40 |
| Group 4 split CALX133ACE 2.5 µg of Ag | <10 | <10 | <10 | <10 | 80 | 160 | 36.67 | 80 |
| Group 5 supernatant Triton X100 2.5 µg | <10 | <10 | <10 | <10 | 40 | 40 | 19.17 | 40 |
| Group 6 supernatant CALX133ACE 2.5 µg | <10 | <10 | <10 | <10 | <10 | 20 | 0.83 | 20 |

The experiment with antigens generated by CALX133ACE fragmentation was validated (good tolerance of the mice, quality and amount of the sera taken, robustness of the HAI results with validated (+) and (−) controls).

The HAI and microneutralization results are coherent and indicate that the antigen split generated by CALX133ACE fragmentation induces a significant antibody response (sample 3 and cardiac puncture), unlike the antigens purified by ultracentrifugation of the splits (denoted "supernatant" in tables III and IV), since these purified antigens are no longer in a membrane context, thereby validating the process for producing and fragmenting the vaccine antigens using the CALX133ACE molecules in qualitative and quantitative terms.

Furthermore, a significant difference emerges in favor of the CALX133ACE process with respect to the Triton X100 process as regards the injected dose at 0.5 µg (sample 3 and cardiac puncture). The same tendency is found with the dose of 2.5 µg, but the difference in HAI is not significant (sample 3 and cardiac puncture).

Furthermore, it appears that the antibody response induced by a dose of 0.5 µg of antigens generated by the CALX133ACE process is similar to that induced with 2.5 µg of antigens generated by the Triton X100 process (sample 3 and cardiac puncture). The latter result is important for the invention since it emphasizes the possibility of obtaining an antibody response with 5 times fewer antigens when they are generated with the CALX133ACE molecule.

Example 4: Immunization of Mice with CALX133ACE: Evaluation in Mice of the Protective Capacity of the Vaccine Antigens Generated In a second experiment, several batches of antigens were produced under the optimal production conditions described above, using Triton X100 or the CALX133ACE molecule as splitting agent. Table V below is a summary of the fragmented materials used for this second animal experiment. It was planned to immunize twice Balb/c mice with the CALX133ACE or Triton X100 antigenic preparations and then to infect them with the A/H1N1 California/7/2009 strain (H1N1 pdm09) in order to verify the protection in the animal.

Group 1: 12 mice (positive control) immunized i.m. (intramuscular) with 1/5 of a dose of Fluviral® (corresponding to 3 µg of HA per antigen).

Group 2: 12 negative control mice ("Ctrl") immunized i.m. with the Triton X100 procedure without antigen (6 mice) or the CALX133ACE procedure without antigen (6 mice).

Group 3: 12 mice immunized i.m. with 3 μg of the HA preparation with Triton X100.

Group 4: 12 mice immunized i.m. with 3 μg of the HA preparation with CALX133ACE.

Group 5: 12 mice immunized i.m. with 0.5 μg of the HA preparation with CALX133ACE.

Figure 1:
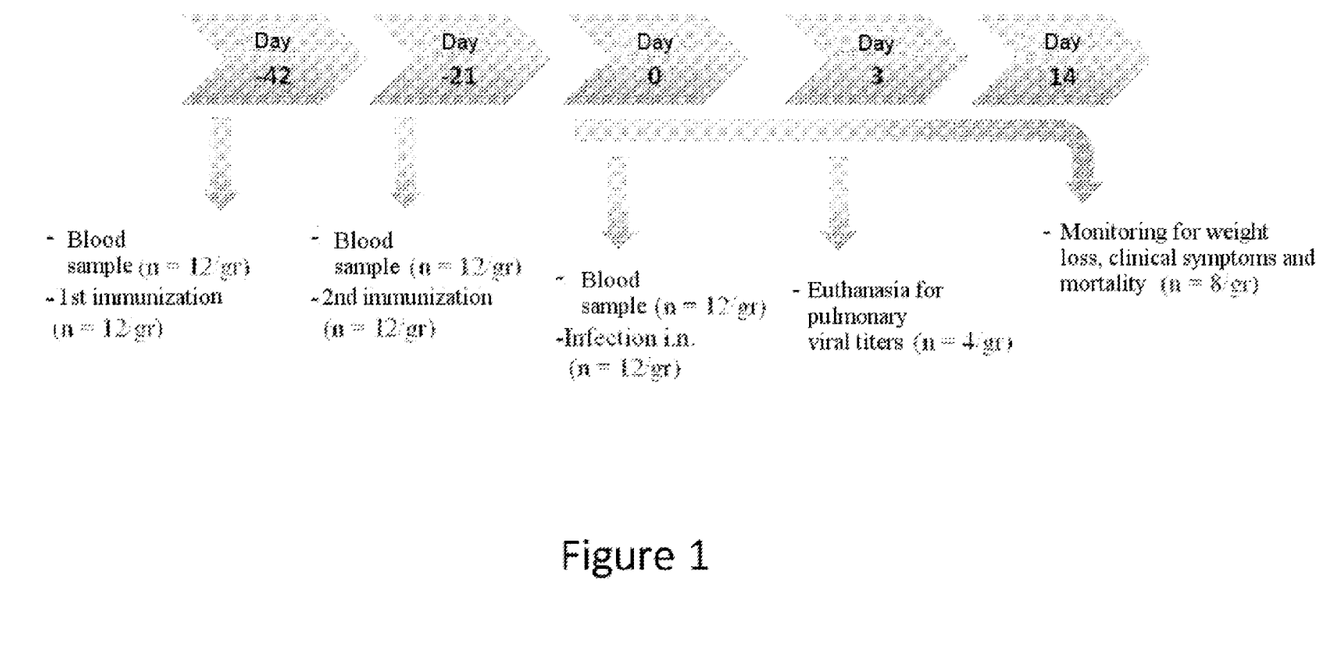
FIG. 1 represents the CALX133ACE immunization protocol with challenge in mice, at D−42 (42 days before the infection), D−21 (21 days before the infection), D0 (day of the infection and of the blood sample), D4 (4 days after the infection) and D14 (14 days after the infection).

The immunization protocol is represented in FIG. 1.

Table V below is a summary of the fragmented materials used for this test.

Figure 4:
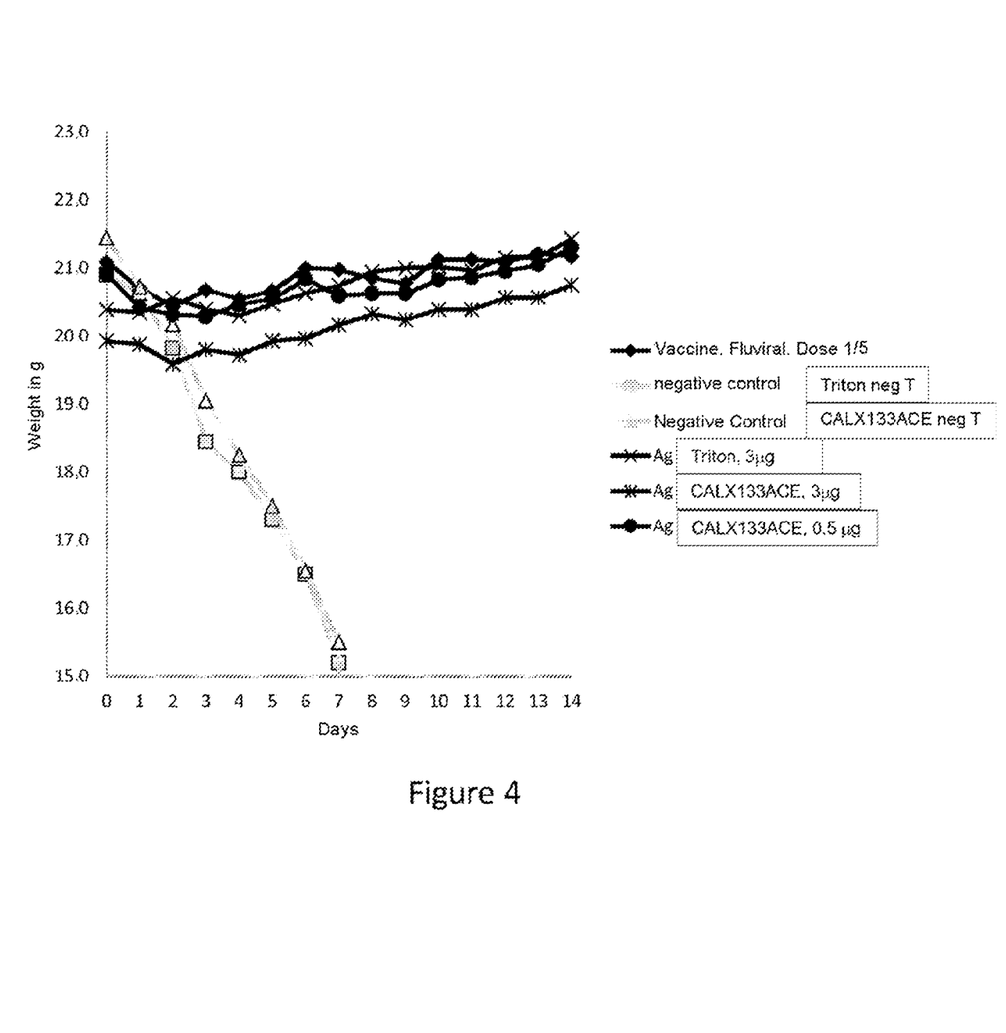
FIG. 4 represents the measurement of weight (in g) of the mice immunized and infected with H1N1 pdm ($10^e3$ IU), from D0 to D14, for the mice to which were administered: the Fluviral® vaccine, dose 1/5 (diamonds), the negative control Triton X100 Neg. C. (squares), the negative control CALX133ACE Neg. C (triangles), 3 µg antigen extracted with Triton X100 (cross), 3 µg antigen extracted with CALX133ACE (star), and 0.5 µg antigen extracted with CALX133ACE (circle).

The weight of the Balb/c mice was monitored after intranasal infection with $10^{e}3$ IU/mouse of influenza virus A H1N1 pdm09 (pandemic) and is described in FIG. 4.

Measurement of the Protection by HAI

The following groups of mice were tested:

mice immunized with the Fluviral® vaccine 1/5, mice immunized with Triton X100 only, mice immunized with CALX133ACE, mice immunized with the viral antigen prepared with Triton X100, 3 μg, mice immunized with the vaccine antigen extracted with CALX133ACE, 3 μg,

TABLE V

| Experimental condition | % of detergent in the crude sample | % of detergent after adjustment | % of detergent injected into the mouse | Approximate sample volume (μl) | HA titer (UHA/50 μl) | [HA] by SRID (μg/ml) | ITRAQ ratio | [HA] corrected by ITRAQ (μg/ml) | Volume to be injected per mouse (μl) For 0.5 μg of Ag | For 3 μg of Ag |
|---|---|---|---|---|---|---|---|---|---|---|
| Split Triton X100 4% | 0.15 | 0.22 | 0.120 | 1650 | 4096 | 108.88 | Split CALX133 ACE/Split Triton X100 T = 0.61 | 108.88 | | 27.55 |
| Split CALX133ACE 1% | 0.03 | 0.03 | 0.004 or 0.022 | 3500 | 16384 | 68.37 | | 82.30 | 6.08 | 36.45 |
| Ctrl-Triton X100 4% | 2 | 0.22 | 0.120 | 850 | — | — | — | — | | 27.55 |
| Ctrl-CALX133ACE 1% | 0.02 | 0.03 | 0.022 | 670 | — | — | — | — | | 36.45 |

The mice were sacrificed on D+4 (virus replication peak), with measurement of their pulmonary viral titer.

The pulmonary viral titer of the mice that were immunized and infected with H1N1 pdm09 ($10^{e}3$ IU), on D+4, was measured after euthanasia and indicated in table VI below.

mice immunized with the vaccine antigen extracted with CALX133ACE, 0.5 μg.

These mice are infected with H1N1 pdm ($10^{e}3$).

The results of the HAI test on the sera of the mice that were immunized and infected with H1N1 pdm ($10^{e}3$) are given in table VI.

TABLE VI

| | | Pulmonary titer | | |
|---|---|---|---|---|
| | Mice | log/ml | pfu/ml | pfu/g |
| Fluviral ® Vaccine 1/5 | 1-9 | <10e2 | | |
| | 1-10 | <10e2 | | |
| | 1-11 | <10e2 | | |
| | 1-12 | <10e2 | | |
| Ctrl Triton X100 | 2-4 | 9 | 9.3 × 10e8 | 4.88 × 10e9 |
| | 2-6 | 8.5 | 2.9 × 10e8 | 1.71 × 10e9 |
| Ctrl CALX133ACE | 2-7 | 7.7 | 5.4 × 10e7 | 3.7 × 10e8 |
| | 2-11 | 8.6 | 4.1 × 10e8 | 2.09 × 10e9 |
| Split Triton X100 3 μg of Ag | 3-1 | <10e2 | | |
| | 3-11* | 4.4 | 2.6 × 10e4 | 1.71 × 10e5 |
| | 3-12 | <10e2 | | |
| Split CALX133ACE 3 μg of Ag | 4-7 | <10e2 | | |
| | 4-8 | <10e2 | | |
| | 4-9 | <10e2 | | |
| | 4-10 | <10e2 | | |
| Split CALX133ACE 0.5 μg of Ag | 5-6 | <10e2 | | |
| | 5-7 | <10e2 | | |
| | 5-8 | <10e2 | | |
| | 5-9 | <10e2 | | |

*Just 1 immunization

TABLE VII

| | | | A/California/7/2009 | | |
|---|---|---|---|---|---|
| | | Number of mice | Preliminary | Sample 2 | Sample 3 |
| Group 1 | Fluviral ® Vaccine 1/5 | 12 | <10 | 20 | 160 |
| Group 2-1 | Ctrl Triton X100 | 6 | <10 | <10 | 10 |
| Group 2-2 | Ctrl CALX133ACE | 6 | <10 | <10 | <10 |
| Group 3-1 | Split Triton X100 3 μg of Ag | 10 | <10 | 10 | 80 |
| Group 4 | Split CALX133ACE 3 μg of Ag | 12 | <10 | 20 | 320 |
| Group 5 | Split CALX133ACE 0.5 μg of Ag | 12 | <10 | 20 | 160 |
| Control + | (A/California) | | 1280 | | |
| Control − | (A/Perth) | | <10 | | |
| | | | D-42 | D-21 | D0 |

Figure 2:
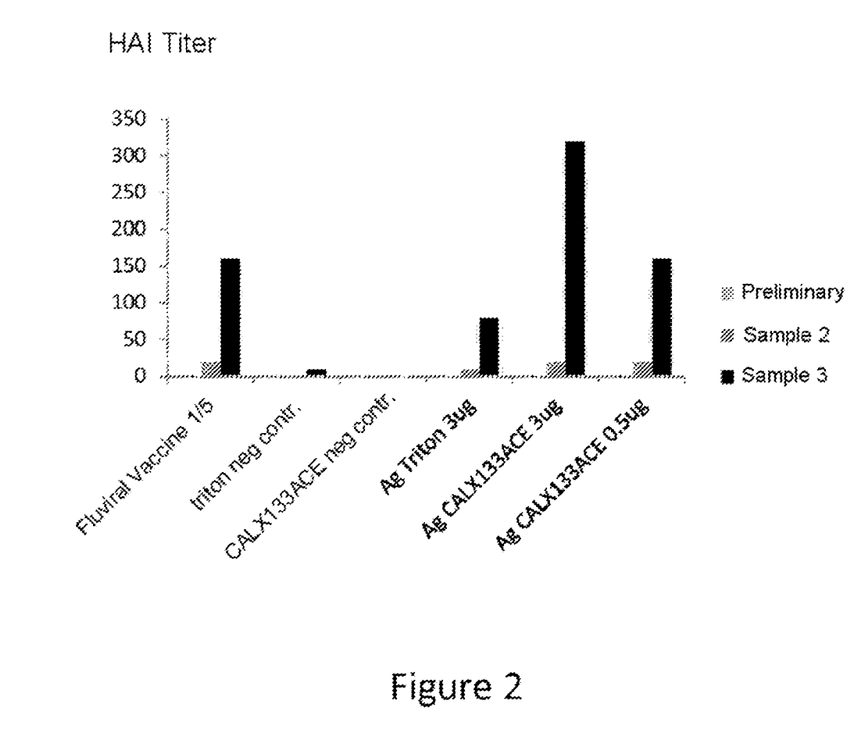
FIG. 2 represents the measurement of the HAI (Hemagglutination Inhibition) titer at D−42 ("Preliminary"), D−21 ("Sample 2") and D0 ("Sample 3"), of mice infected with H1N1 pdm ($10^e3$) and optionally immunized with (from left to right): Fluviral® 1/5 vaccine, Triton X100 negative control, CALX133ACE negative control, 3 µg antigen Triton X100, 3 µg antigen-1 dose Triton X100, 3 µg antigen CALX133ACE and 0.5 µg antigen CALX133ACE.

The measurement of the protection by HAI is shown in FIG. 2.

Measurement of the Protection by MN (Microneutralization)

The following groups of mice are tested:

mice immunized with the Fluviral® vaccine 1/5, mice immunized with Triton X100 only, mice immunized with CALX133ACE, mice immunized with the viral antigen prepared with Triton X100, 3 µg, mice immunized with the vaccine antigen extracted with CALX133AC, 3 µg mice immunized with the vaccine antigen extracted with CALX133ACE, 0.5 µg.

These mice are infected with H1N1 pdm ($10^3$).

The MN tests on the sera of the mice that were immunized and infected with H1N1 pdm ($10^3$) are summarized in table VIII below.

TABLE VIII

| | | Number of mice | 17 Jun. 2014 A/California/7/2009 | | |
|---|---|---|---|---|---|
| | | | Preliminary | Sample 2 | Sample 3 |
| Group 1 | Fluviral Vaccine 1/5 | 12 | <10 | 20 | 160 |
| Group 2-1 | Ctrl Triton X100 | 6 | <10 | <10 | <10 |
| Group 2-2 | Ctrl CALX133ACE | 6 | <10 | <10 | <10 |
| Group 3-1 | Split Triton X100 3 µg of Ag | 10 | <10 | 20 | 40 |
| Group 4 | Split CALX133ACE 3 µg of Ag | 12 | <10 | 20 | 320 |
| Group 5 | Split CALX133ACE 0.5 µg of Ag | 12 | <10 | 20 | 160 |
| | | | D-42 | D-21 | D0 |

Figure 3:
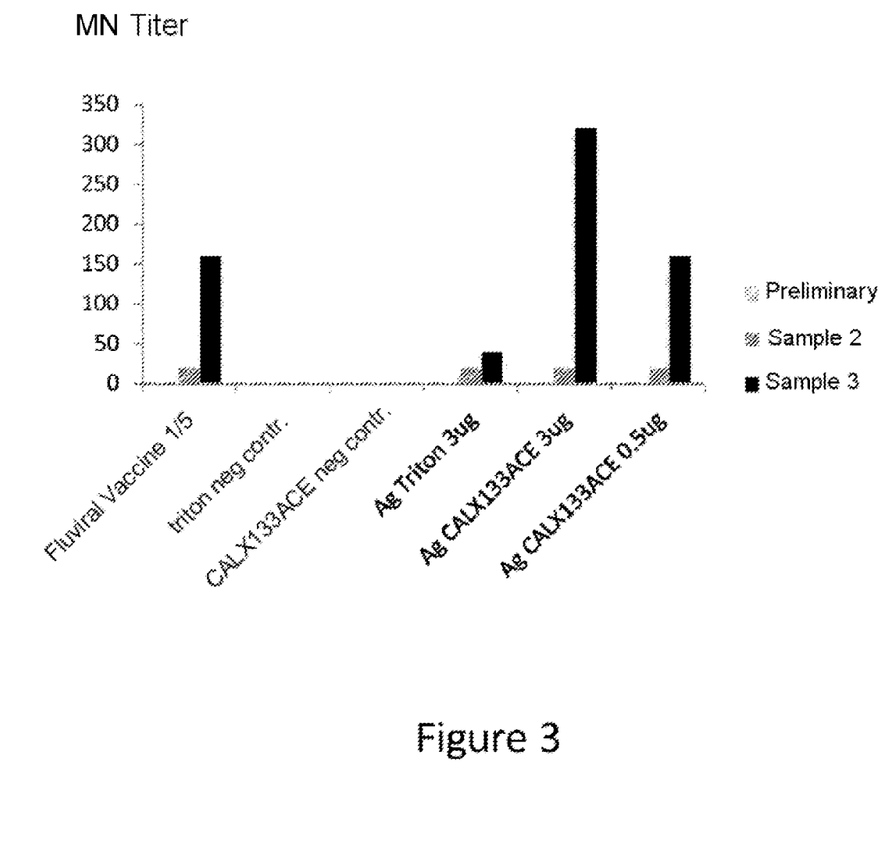
FIG. 3 represents the measurement of the MN (microneutralization) titer at D−42 ("Preliminary"), D−21 ("Sample 2") and D0 ("Sample 3"), of mice infected with H1N1 pdm ($10^e3$) and optionally immunized with (from left to right): Fluviral® 1/5 vaccine, Triton X100 negative control, CALX133ACE negative control, 3 µg antigen Triton X100, 3 µg antigen-1 dose Triton X100, 3 µg CALX133ACE antigen and 0.5 µg CALX133ACE antigen.

The measurement of the protection by MN is shown in FIG. 3.

Protection of the Mice

FIG. 5 represents the monitoring of the weight of the mice that were immunized and infected with H1N1 pdm ($10^3$ IU).

In all the immunized groups (Fluviral, Triton X100 and CALX133ACE): no weight loss or mortality.

Only the mice in the 2 negative control groups died.

CONCLUSION

HAI and MN Tests:

The immunization is as effective with 0.5 µg of antigen split/CALX133ACE as with 3 µg of Fluviral®.

The immunization is more effective with 3 µg of antigen split/CALX133ACE as with 3 µg of antigen split/Triton X100.

Protection:

The protection is as effective with 0.5 µg of antigen split/CALX133ACE as with 3 µg of Fluviral or 3 µg of antigen split/Triton X100.

The invention claimed is:

1. A process for preparing a vaccine antigen, comprising a step of fragmenting a biological membrane associated with said vaccine antigen by bringing said biological membrane into contact with at least one calixarene of formula (II):

in which:

X is a $(CH_2)$—$CO_2Y$ group, and

Y is an alkali metal, or a pharmaceutically acceptable salt thereof, wherein said vaccine antigen obtained also comprises a fragment of the biological membrane, said fragment being associated with said antigen, and wherein the vaccine antigen is a membrane protein of flu virus.

2. The process as claimed in claim 1, wherein Y is sodium.

3. The process as claimed in claim 1, wherein said biological membrane is derived from the flu virus.

4. The process as claimed in claim 1, wherein said biological membrane is derived from an embryonated egg.

5. The process as claimed in claim 1, wherein said vaccine antigen comprises a biological membrane of the flu virus.

6. The process as claimed in claim 1, wherein said viral origin is chosen from the group comprising: the orthomyxoviridae virus family and the paramyxoviridae virus family.

7. The process as claimed in claim 6, wherein said flu virus is chosen from influenza viruses A and influenza viruses B.

8. The process as claimed in claim 1, also comprising a step of dialyzing said vaccine antigen.

9. A vaccine that can be produced by carrying out the process as defined in claim 1, comprising a calixarene of formula (II) in excipient format in an amount of from 0.1 to 1000 µg in the total weight of the vaccine.

10. The vaccine as claimed in claim 9, for application thereof as a medicament in the treatment or prevention of an infectious disease.

11. A process for preparing a vaccine antigen, consisting of a step of fragmenting a biological membrane associated with said vaccine antigen by bringing said biological membrane into contact with at least one calixarene of formula (II):

(II)

in which:
  X is a (CH$_2$)—CO$_2$Y group, and
  Y is an alkali metal,
or a pharmaceutically acceptable salt thereof,
wherein said vaccine antigen obtained also comprises a fragment of the biological membrane, said fragment being associated with said antigen, and
wherein the vaccine antigen is a membrane protein of flu virus.

* * * * *